(12) United States Patent
Xu et al.

(10) Patent No.: US 11,648,015 B2
(45) Date of Patent: May 16, 2023

(54) WATERJET CUTTING SYSTEM

(71) Applicant: Zimmer, Inc., Warsaw, IN (US)

(72) Inventors: Zhiyong Xu, Warsaw, IN (US); Zixin Li, Warsaw, IN (US); Weihao Wang, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 131 days.

(21) Appl. No.: 16/644,423

(22) PCT Filed: Sep. 21, 2017

(86) PCT No.: PCT/CN2017/102612
§ 371 (c)(1),
(2) Date: Mar. 4, 2020

(87) PCT Pub. No.: WO2019/056248
PCT Pub. Date: Mar. 28, 2019

(65) Prior Publication Data
US 2020/0214720 A1 Jul. 9, 2020

(51) Int. Cl.
*A61B 17/15* (2006.01)
*A61B 34/10* (2016.01)
(Continued)

(52) U.S. Cl.
CPC .......... *A61B 17/155* (2013.01); *A61B 17/157* (2013.01); *A61B 17/1764* (2013.01); *A61B 2017/1648* (2013.01); *A61B 2034/105* (2016.02); *A61B 2034/108* (2016.02)

(58) Field of Classification Search
CPC combination set(s) only.
See application file for complete search history.

(56) References Cited

U.S. PATENT DOCUMENTS

| 5,234,433 A | 8/1993 | Bert et al. |
| 6,893,425 B2 | 5/2005 | Dunn et al. |
| (Continued) | | |

FOREIGN PATENT DOCUMENTS

| CN | 104039252 | 9/2014 |
| CN | 104379074 | 2/2015 |
| (Continued) | | |

OTHER PUBLICATIONS

"International Application Serial No. PCT/CN2017/102612, International Search Report dated Jun. 15, 2018", 7 pgs.
(Continued)

*Primary Examiner* — Sameh R Boles
(74) *Attorney, Agent, or Firm* — Schwegman Lundberg & Woessner, P.A.

(57) ABSTRACT

Systems (100, 900, 1100), devices, and methods may be used to print or use a patient-specific waterjet cut guide (104, 302, 902, 1102). A method may include receiving, at a processor, image data of a bone (102, 308) of a patient (702), rendering a model of the bone (102, 308) (704) and generating a cut guide model using the model of the bone (102, 308) (706). The method may include printing, using a three-dimensional (3D) printer, a waterjet cut guide (104, 302, 902, 1102) using the cut guide model. A method may include using the patient-specific waterjet cut guide (104, 302, 902, 1102) to perform a resection using a waterjet cutting device, the waterjet cutting device including a nozzle (108, 306, 406, 500A, 500B) insertable into a cut guide slot (106B, 304, 310, 906, 1104) of the patient-specific waterjet cut guide (104, 302, 902, 1102).

8 Claims, 11 Drawing Sheets

(51) Int. Cl.
  *A61B 17/17* (2006.01)
  *A61B 17/16* (2006.01)

(56) References Cited

U.S. PATENT DOCUMENTS

| | | | |
|---|---|---|---|
| 8,313,490 | B2 | 11/2012 | May |
| 8,591,516 | B2 | 11/2013 | Metzger et al. |
| 9,060,786 | B2 | 6/2015 | Uthgenannt et al. |
| 2004/0143269 | A1 | 7/2004 | Pude et al. |
| 2008/0243127 | A1 | 10/2008 | Lang et al. |
| 2013/0006250 | A1 | 1/2013 | Metzger et al. |
| 2013/0012949 | A1 | 1/2013 | Fallin et al. |
| 2016/0022370 | A1 | 1/2016 | Pavlovskaia et al. |
| 2016/0192949 | A1* | 7/2016 | Robichaud ......... A61B 17/1735 606/87 |

FOREIGN PATENT DOCUMENTS

| | | | |
|---|---|---|---|
| CN | 104783861 | A | 7/2015 |
| CN | 104997547 | A | 10/2015 |
| CN | 205339051 | U | 6/2016 |
| CN | 106264671 | A | 1/2017 |
| CN | 111263616 | A | 6/2020 |
| DE | 20213570.5 | | 11/2002 |
| EP | 1574170 | A1 | 9/2005 |
| WO | WO-2007101015 | A1 | 9/2007 |
| WO | WO-2017008032 | A1 | 1/2017 |
| WO | WO-2019056248 | A1 | 3/2019 |

OTHER PUBLICATIONS

"International Application Serial No. PCT/CN2017/102612, Written Opinion dated Jun. 15, 2018", 5 pgs.

"European Application Serial No. 17925993.2, Extended European Search Report dated Apr. 16, 2021", 10 pgs.

"Chinese Application Serial No. 201780095065.0, Office Action dated Sep. 23, 2022", w English translation, 16 pgs.

"Chinese Application Serial No. 201780095065.0, Response filed Dec. 26, 2022 to Office Action dated Sep. 23, 2022", w English claims, 12 pgs.

* cited by examiner

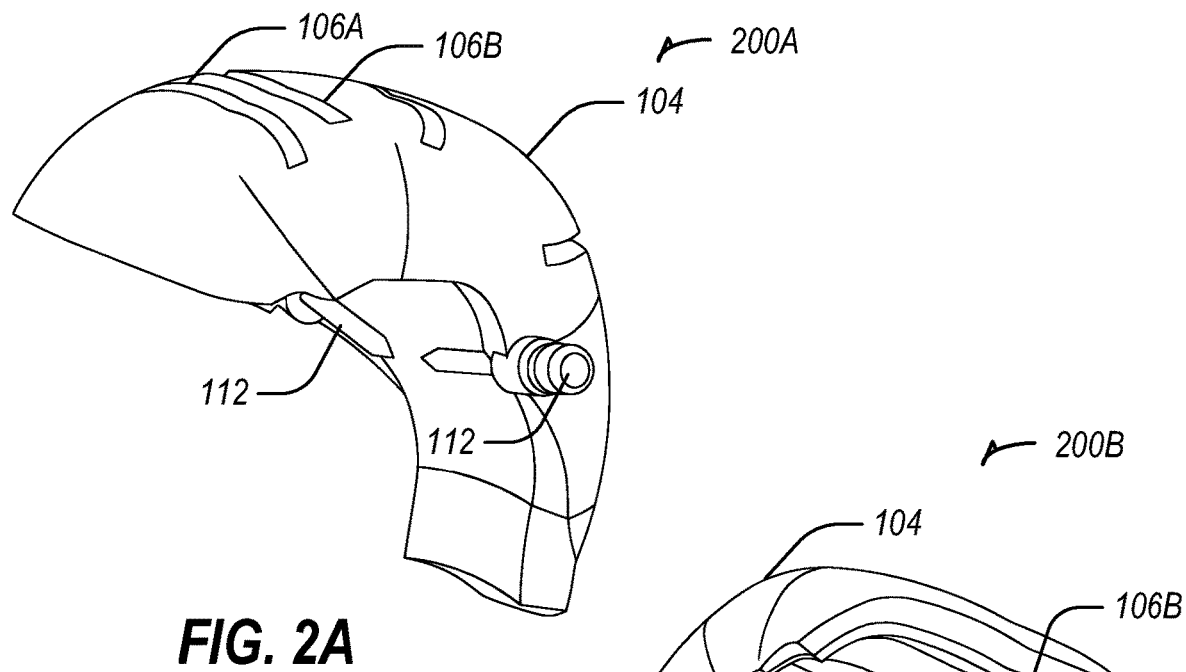
FIG. 2A
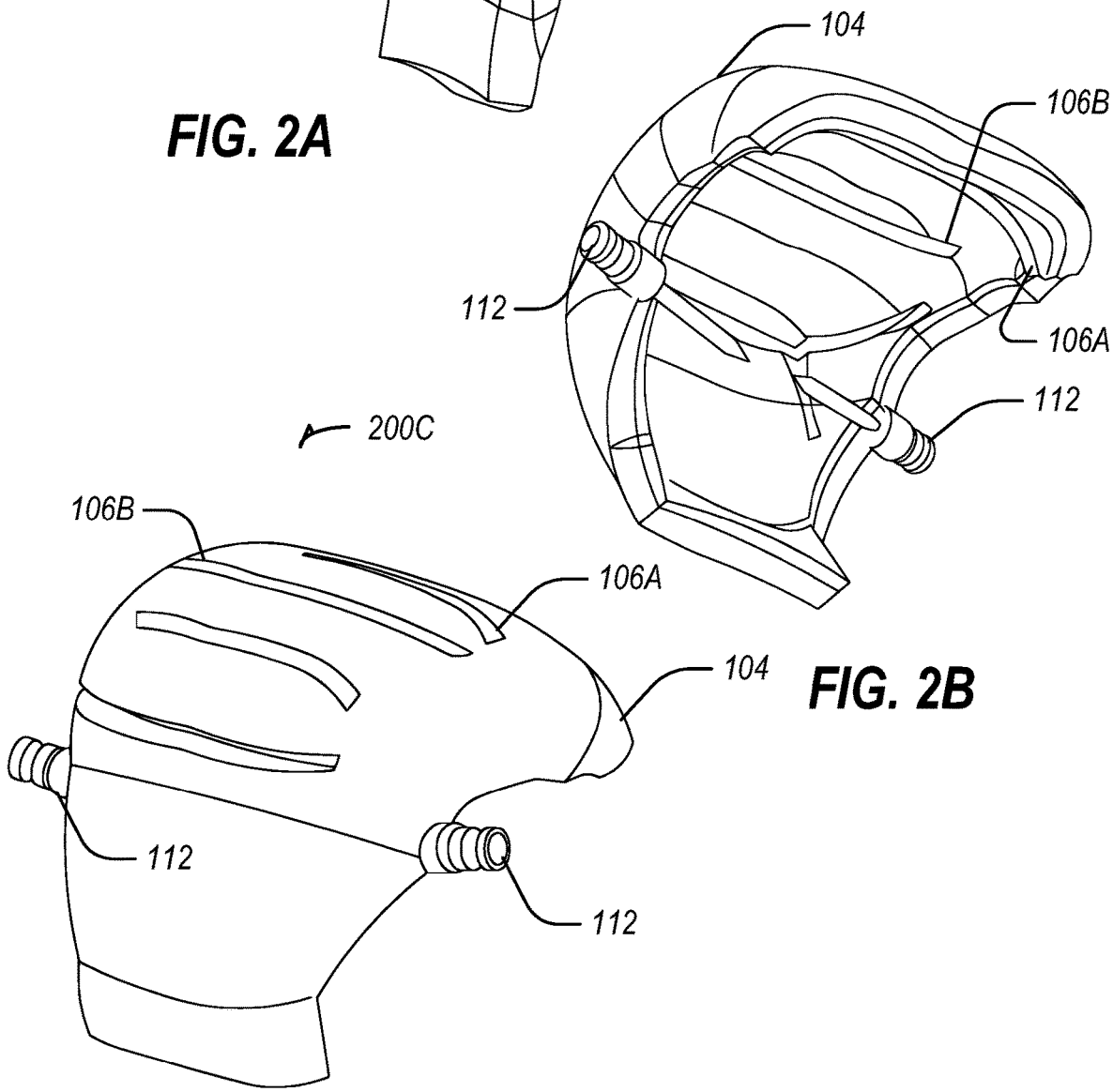
FIG. 2B
FIG. 2C

WATERJET CUTTING SYSTEM

This application is a U.S. National Stage Application under 35 U.S.C. 371 from International Application Serial No. PCT/CN2017/102612, filed on Sep. 21, 2017, and published as WO 2019/056248 A1 on Mar. 28, 2019, the benefit of priority of which is claimed hereby, and which is incorporated by reference herein in its entirety.

BACKGROUND

A cut guide is used in orthopedic surgery to align a cutting, burring, or sawing device with a target object. A cut guide is useful for planning out a cut and allowing for the cut to be precise even in the presence of vibration or movement of the cutting device. However, the cut guide is sometimes placed imprecisely due to patient movement, lack of experience, or obstructed visual access. Further, some traditional cutting techniques rely on a sawblade, which may be imprecise or accidentally damage bone or soft tissue. For example, resistance in a bone when being cut by a sawblade, such as due to changes in density or hardness of the bone, may cause skiving, where the sawblade moves in an unexpected or undesirable direction, which results in inaccuracies in the cut.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 2A-2C illustrate three views of waterjet cut guide in accordance with some embodiments.

DETAILED DESCRIPTION

Figure 1:
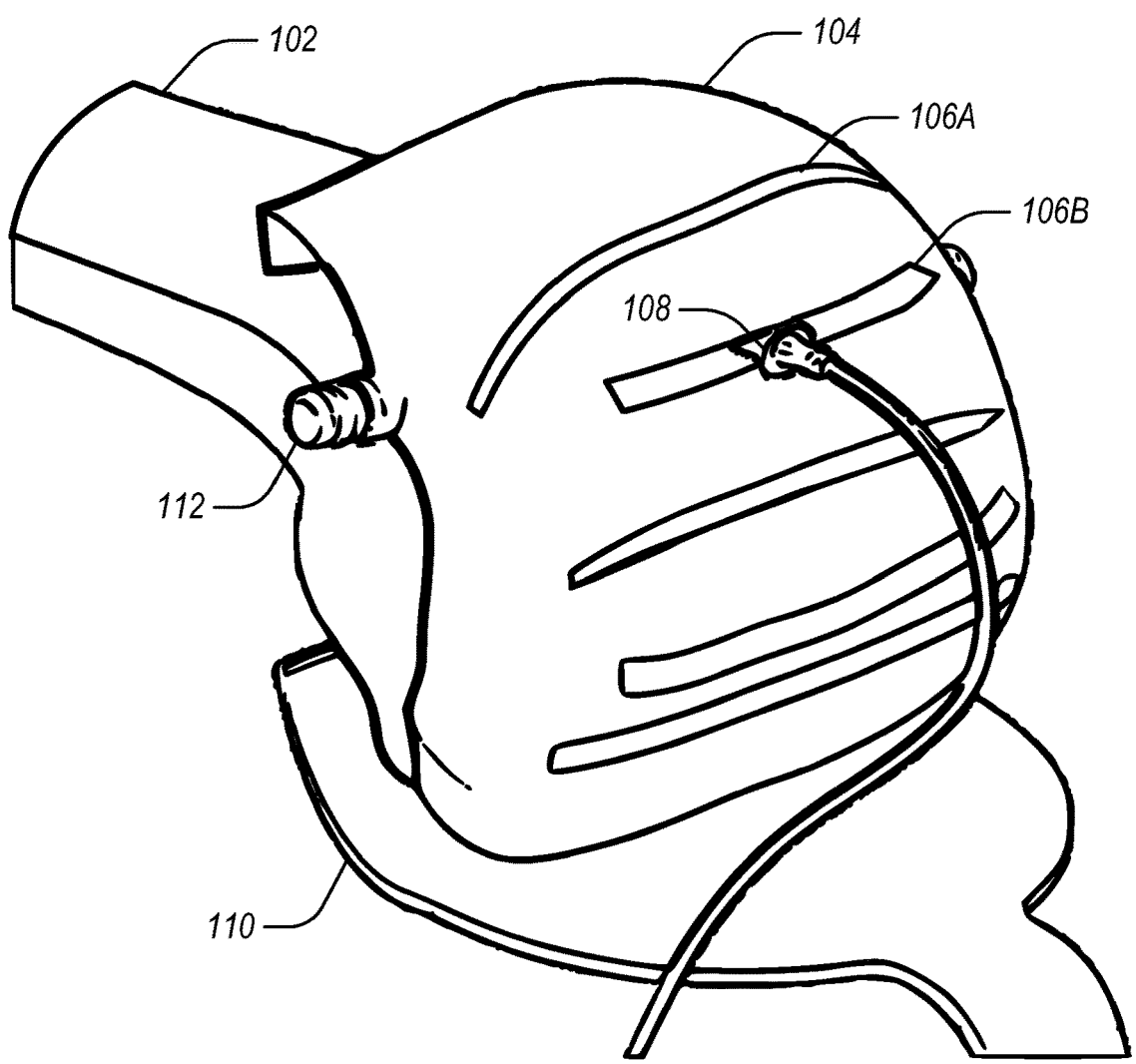
FIG. 1 illustrates a waterjet cutting system in accordance with some embodiments.

In certain orthopedic procedures, a cut guide is used to allow a surgeon to resect a bone, for example a femur or a tibia, such as during a total or partial knee arthroplasty. A cut guide may be sized as part of a set of cut guides, or may be customized to a patient. Customizing the cut guide may include using a three-dimensional (3D) model (e.g., from an x-ray, CT scan, MRI, etc.) to generate a custom cut guide.

A surgeon may use a cut guide to allow a cutting device to perform resections or other cuts of a bone. For example, the cut guide may include one or more slots for a cutting device to be inserted into for cutting the bone. In an example, a cut guide may include a number of slots to complete a surgical procedure without moving the cut guide.

A cutting device typically used during surgical procedures to cut bone may include a sawblade, a burr, a rasp, a reamer, or the like. These devices include a solid cutting element attached to a handle portion. In another example, a cutting device may be a waterjet cutting device, for example including a tubular portion to convey water to a nozzle portion. The waterjet cutting device may use pure water or a mixture of water and one or more additional materials, such as an abrasive substance (e.g., garnet, cement, etc.). The nozzle portion ejects water at a high pressure in a defined shape, typically a thin line. In an example, the high pressure water is used to cut bone, and the water exiting the nozzle is sufficiently pressurized to cut through the bone. In an example, the pressure sufficient to cut through the bone may vary depending on the bone to be cut, attributes of the bone (e.g., density, calcification, etc.), whether the water is pure water or mixed with additional material, such as an abrasive (which may use a lower sufficient pressure while still cutting the bone), distance from the nozzle to the bone, or the like. The nozzle may expel a pressurized cutting fluid in a defined shape.

The systems and methods described herein include a waterjet cutting system for resecting a femur, tibia, or other bone. The waterjet cutting system uses a waterjet cutting device, including a nozzle, and a cut guide. In an example, the waterjet cutting system includes a protection plate to protect adjacent tissues during resection. The cut guide may include a printed cut guide, such as a 3D cut guide printed using a 3D printing technique or similar additive manufacturing method. For example, a model may be created using a 3D modeler (e.g., from a patient image such as an X-ray, a CT scan, or a MRI), which may then be sent to a 3D printer. For example, CT scan images may be used to create measurements to create the 3D printed cut guide. The 3D cut guide may be printed in metal using the 3D printer or formed through an additive manufacturing process such as laser sintering. The 3D cut guide may be customized to a patient.

Once printed, the 3D cut guide may be placed on a target bone of a patient to be used to guide the nozzle of the waterjet cutting device. The nozzle may be inserted into a slot of the 3D cut guide and the waterjet cutting device may be activated. Once activated, the waterjet cutting device may send pressurized water (e.g., pure water or a mixture, such as water with an abrasive, such as cement particles as a water-cement mixture or garnet for a water-garnet mixture) through a tubular portion of the waterjet cutting device to the nozzle, which may eject the water towards the bone, through the slot. The water cuts the bone, and the nozzle may be adjusted or moved, such as by a surgeon to complete a cut. For example, the nozzle may be rotated relative to the 3D cut guide to allow for a cut along a plane parallel to the slot.

The waterjet cutting system described herein uses a 3D-printing technique to create a 3D-printed cut guide for use with a waterjet cutting device. The 3D-printed cut guide may be made of a rigid material such as metal or plastic, and may be customized to anatomy of a patient. The 3D-printed cut guide may be printed as a single piece or may be printed in parts (e.g., in two symmetrical or semi-symmetrical lateral parts that may be fit together over a bone). When printed in parts, the 3D-printed cut guide may be printed with a lateral part and a medial part or an anterior part and a posterior part, or may be split into more than two pieces. The parts may be coupled together to create the full 3D-printed cut guide, such as using a locking mechanism, glue, or by being affixed to a bone (e.g., using pins). A 3D-printed cut guide may be printed using patient-specific cut guide techniques for imaging, modeling or preparing for printing, such as those described in U.S. Pat. No. 8,591,516, titled Patient-Specific Orthopedic Instruments, which is incorporated herein in its entirety.

In an example, the waterjet cutting system described herein may protect a patient's bone during resection from heating damage typically associated with cuts in procedures, such as a knee arthroplasty. For example, some cutting devices may cause heat to be transferred to the bone, such as by a cutting device (e.g., a saw or a burr) vibrating and friction. The waterjet cutting system described herein may provide a personalized cut guide, which may produce better results (e.g., more precise cuts, less recovery time, reduced operating time for a procedure, fewer refining cuts, less damage to the bone based on the waterjet technique, etc.) than with a non-personalized cut guide or a one-size-fits-all type of cut guide.

FIG. 1 illustrates a waterjet cutting system 100 in accordance with some embodiments. The waterjet cutting system 100 includes a cut guide 104, which may be affixed or arranged about a bone 102, for example using one or more pins or screws (e.g., pin 112). The cut guide 104 may include one or more slots (e.g., slot 106A-106B), which may be configured to receive a nozzle 108 of a waterjet cutting device. The waterjet cutting system 100 may include a plate 110, which may be affixed to the cut guide 104 or may be separate from the cut guide 104. The plate 110 may be manufactured with the cut guide 104 (e.g., both as a single piece), may be manufactured in two or more pieces, or may be manufactured as a single standalone piece. As a standalone piece, the plate 110 can be positioned by the surgeon or assistant during the procedure to protect adjacent tissues during resection of the target bone.

The cut guide 104 may be custom to a patient. For example, the cut guide 104 may be printed using a 3D printer based on a model. The model may be creating using data from the patient, such as an X-Ray, a CT scan or an MRI of the patient. The model may use measurements, such as of the patient's size, the angle of limb alignment (e.g., femur to tibia limb alignment), soft tissue tension, etc. The cut guide 104 may be printed using the model based on X-Ray, CT, or MRI data and measured data.

In an example, the cut guide 104 is affixed to the bone 102 using the pin 112. An additional pin opposite the pin 112 may be used to secure the cut guide 104 to the bone 102. To prevent the cut guide 104 from rotating around the axis of the pin 112, the cut guide 104 may be in contact with the bone 102 in at least one additional location to prevent rotation. In an example, the plate 110 may be used to prevent rotation of the cut guide 104 with respect to the bone 102. The plate 110 may be secured by a variety of techniques. For example, a surgical assistant may hold the plate 110. In another example, the plate 110 may be secured between the bone 102, when the bone 102 is a femur, and a tibia, for example making use of soft tissue (e.g. ligaments) connecting the femur to the tibia or force from the cut guide 104 towards the tibia to keep the plate 110 in compression. Friction on the plate 110 from the femur, the tibia, or the cut guide 104 may prevent the plate 110 from moving while the cut guide 104 is compressed. In an example, friction between the plate 110 and the cut guide 104 may prevent the cut guide 104 from rotating. In yet another example, the plate 110 may be secured to the patient, such as the bone 102, the tibia, etc. The cut guide 104 or the plate 110 may be generated using x-ray imaging to generate a patient-specific instrument cut guide or plate. For example, the techniques described in U.S. Pat. No. 9,060,786, titled "X-Ray Based Cutblock Positioning Jig," which is hereby incorporated herein in its entirety, may be used to generate an x-ray-based patient-specific instrument.

The plate 110 may be made of metal, such as steel or other material used to prevent the water cutting device from cutting through a tibia, soft tissue, or other aspects of the patient or the surgical field. In an example, the plate 110 is curved, which may prevent the water cutting device from cutting behind the bone 102. The nozzle 108 may eject water or a water mixture in a straight or substantially straight line, such as by ejecting water or water mixture out of the nozzle 108. The nozzle may expel a pressurized cutting fluid in a defined shape.

The ejected water or water mixture may be a circular column, a thin line (e.g., a spray of water), a u-shape, or the like. For example, the circular column may be used to perform precise cuts, such as by rotating or moving the nozzle 108 throughout the slot 106B. The thin line or spray may be used to perform a cut quickly, such as by spraying a line of water throughout the slot 106B, where the cut may be made without rotating or moving the nozzle 108. The u-shape or other shaped water ejecta may be used to avoid portions of the bone or soft tissue when cutting. In an example, the water ejected from the nozzle 108 may include portions of higher water pressure such that the nozzle 108 may cut through the bone 102 evenly when the bone has calcified portions or other harder or denser material. The higher pressure portions of the ejecta may be used to target the harder or denser material while lower pressure portions of the ejecta are used to cut through less hard or dense material of the bone 102. In another example, the pressure of the water may be changed while the nozzle 108 is moved or rotated within the slot 106B.

In an example, a nozzle head of the nozzle 108 may be shaped to control the flow of water or water mixture from the nozzle 108. For example, to achieve the spray, a wide nozzle head may be used. To achieve a column of water, a circular nozzle head may be used. In an example, multiple nozzle heads may be used. For example, nozzle heads may be removable and interchangeable, such that a first type of nozzle head may be used for a first cut and a second type may be used for a second cut. In an example, multiple nozzles may be used concurrently. For example, an array of nozzles may be used to perform a cut more quickly than when using a single nozzle. The flow rate, pressure, nozzle type, ejecta type, direction, angle, or movement of the nozzle 108 and the waterjet cutting system 100 in general may be surgeon-controlled. For example, an apparatus (e.g., to control a valve) may be attached to the waterjet cutting device to allow the surgeon to alter the flow rate. In another example, a computer system may be used to control aspects of the waterjet cutting system 100, such as flow rate or pressure of water ejected from the nozzle 108. In yet another example, the nozzle 108 shape may be controlled electro-mechanically. For example, the shape of the nozzle 108 may be changed according to a desired output by adjusting a physical aspect of the nozzle 108, such as by narrowing or expanding an opening, changing the shape by increasing a curvature of the nozzle 108, etc.

The nozzle 108 may impart an angular momentum to the water or water mixture to keep the water or water mixture in the circular column after exiting the nozzle 108. In an example, the plate 110 may have a seesaw shape to protect aspects of the patient (e.g., soft tissue, bone, etc.) from being cut by the waterjet cutting device. For example, the seesaw shape of the plate 110 may be used for protection when performing a posterior condyle cut or a posterior chamfer cut. These cuts may be performed by inserting the nozzle 108 into corresponding slots on the cut guide 104.

FIGS. 2A-2C illustrate three views 200A-200C of a waterjet cut guide in accordance with some embodiments. FIG. 2A includes a first side view 200A, FIG. 2B includes a bottom-up view 200B, and FIG. 2C includes a second side view 200C. The waterjet cut guide illustrated in FIGS. 2A-2C may be a 3D cut guide, printed with a 3D printer as described herein. In an example, the waterjet cut guide shown in FIGS. 2A-2C may be built based on features of a patient's distal femur or limb alignment. The waterjet cut guide may be directly placed on the distal femur and may be printed to fit on the distal femur of the particular patient (e.g., customized to the patient). The bottom-up view 200B shows a surface that may rest directly on the distal femur. By 3D printing a custom waterjet cut guide for a particular patient, repeated fixing of the cut guide on the patient's femur may be avoided.

After the cut guide is coupled to the bone, it may be affixed to the bone, for example using compression (e.g., 3D printing the cut guide to have an interference fit with the bone, for example by having a negative allowance between the bone and the cut guide), with pins or screws, with surgical glue, etc. After the cut guide is fixed to the bone, a nozzle may be inserted into the one of a plurality of slots of the cut guide. Each slot may correspond to a cut to be made on the bone, and the nozzle may be moved through each slot to complete the cuts. For example, the nozzle may complete five bone resurfaces of a femur. Use of the waterjet cut guide may help reduce the time spent during a procedure or operation and may prevent cutting error, which would otherwise be caused by repeated fixing.

Figure 3A:
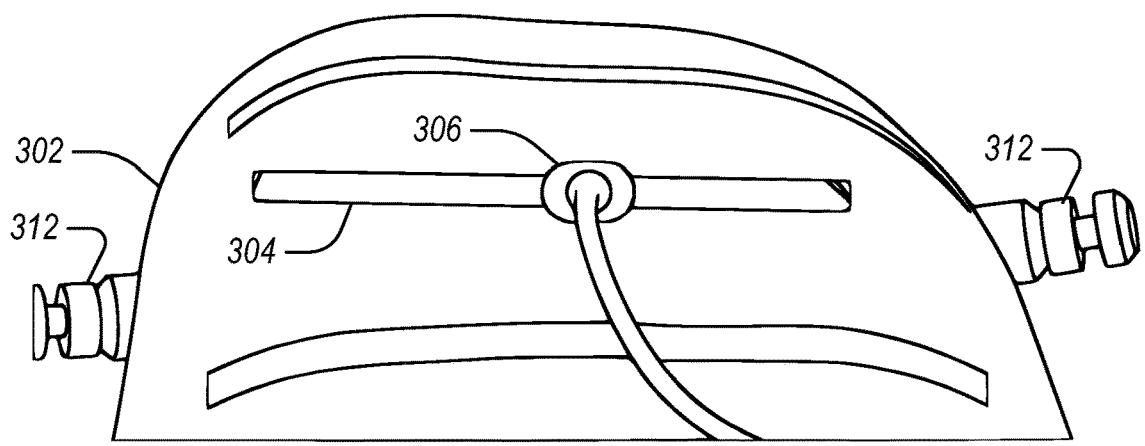
FIGS. 3A-3B illustrate two views of an anterior condyle cut arrangement for using a waterjet cutting system in accordance with some embodiments.
Figure 3B:
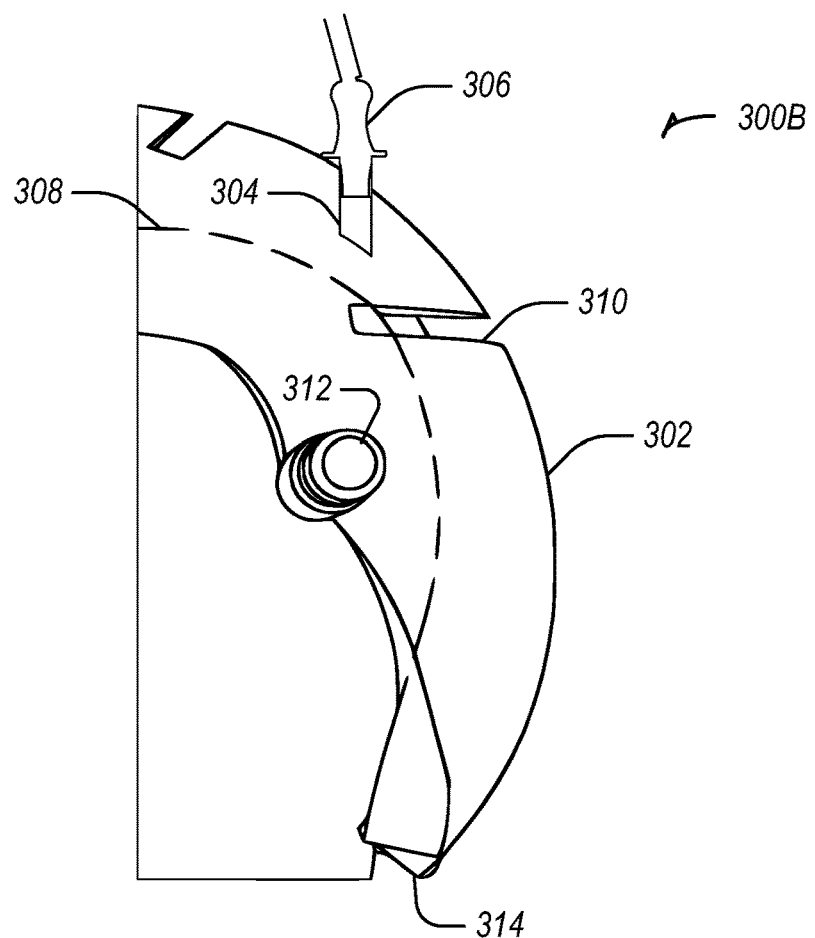

FIGS. 3A-3B illustrate two views of an anterior condyle cut arrangement for using a waterjet cutting system in accordance with some embodiments. FIG. 3A illustrates a front view 300A of a cut guide 302 with a slot 304 configured to receive a nozzle 306 of a waterjet cutting device. FIG. 3B illustrates a side view 300B of the cut guide 302 and the nozzle 306, as well as an aspect of a bone 308 to be cut that is partially hidden by the cut guide 302. The nozzle 306 may eject water or a water mixture to cut through the bone 308 when the nozzle is inserted into the slot 304. In an example, the nozzle 306 may be moved to a second slot 310 to perform a second cut on the bone 308. Other slots may be used to make other cuts. The bone 308 may be a femur, and the cuts may be performed as part of a knee arthroplasty.

The cut guide 302 of FIGS. 3A and 3B may be modeled, designed, and printed such that the shape of the cut guide 302 protects portions of the bone 308 (that are not intended to be cut) from being cut when a resection is made with a waterjet cutting device using the nozzle 306. For example, when an anterior resection is made (e.g., during a knee arthroplasty), anterior chamfers of the bone 308 may be protected from a waterjet ejection by the cut guide 302. In another example, distal or posterior chamfers of the femur may be protected by the cut guide 302 when a resection is made. In yet another example, when the cut guide 302 is used with a tibia to make a proximal tibial cut, the cut guide 302 may protect other portions of the tibia. The cut guide 302 may offer protection to the bone 308, such as at locations of the cut guide 302 that extend around the bone 308 (e.g., the portion near the pins 312, or an extended portion 314). For example, the extended portion 314 may stop ejecta from the nozzle 306 to prevent the ejecta from cutting soft tissue or other portions of the bone 308 after a desired resection of the bone 308 is completed, for example, a cut made with the nozzle 306 in the slot 304 as shown in FIG. 3B.

Figure 4:
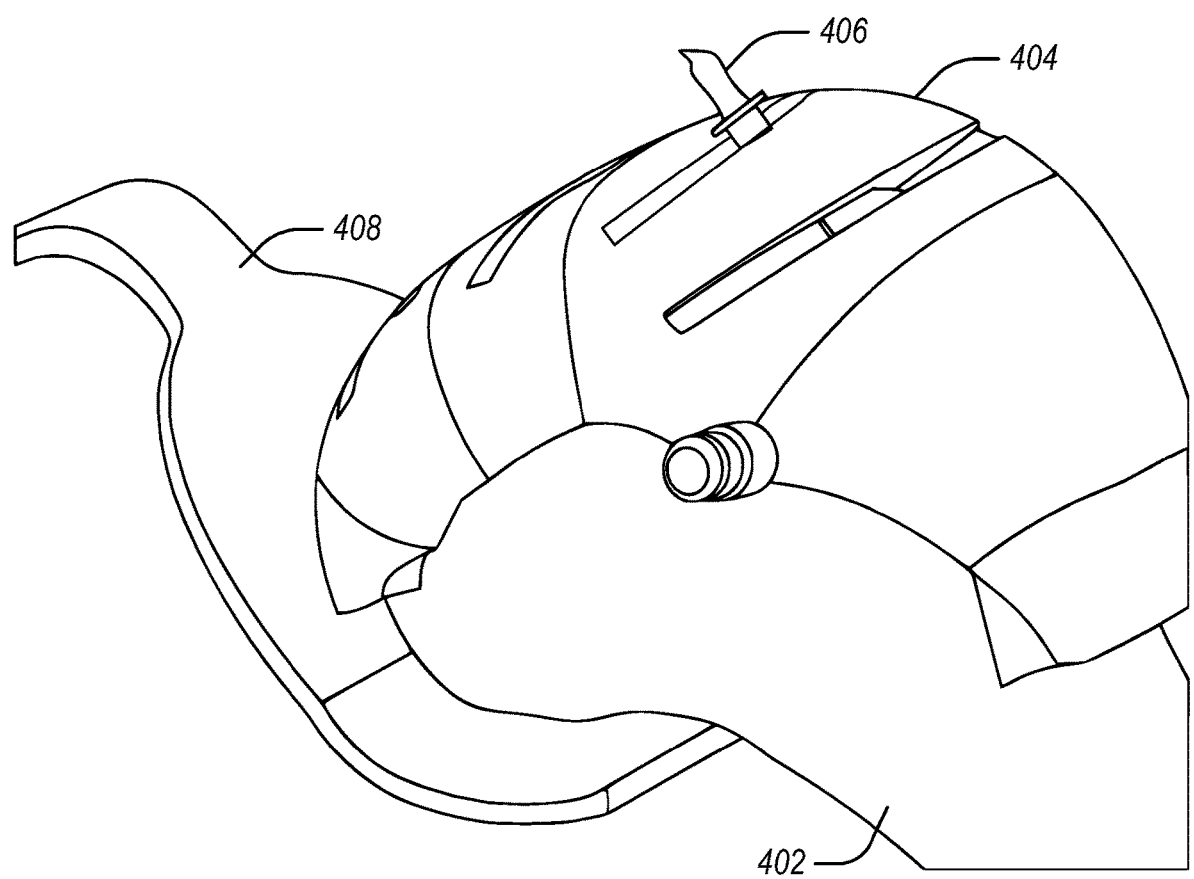
FIG. 4 illustrates protection plate for use with a waterjet cutting system in accordance with some embodiments.

FIG. 4 illustrates a protection plate 408 for use with a waterjet cutting system 400 in accordance with some embodiments. The protection plate 408 may be used to stop water or water mixture ejected from the nozzle 406 after it has cut a bone 402 as the water or water mixture hits the protection plate 408, such as to prevent the water or water mixture from cutting through soft tissue or bone. Aspects of a surgical field often have limited operation space for performing a procedure. For example, during a knee arthroplasty, a cut to be performed may be along a line through the a slot of a cut guide 404 into a femur (bone 402). The line may continue into soft tissue or a tibia or other aspects of a patient or the surgical field that are not to be cut. The protection plate 408 may fit within the limited space and protect the other patient anatomy from being cut. The protection plate 408 may be a metal plate with a handle, and may be used to protect the body organization from the waterjet, such as when the nozzle 406 is used to perform a posterior condyle cut or a posterior chamfer cut.

In an example, one side of the protection plate 408 may contact a proximal tibial plane and act as a fulcrum, and an opposite side may lever up the femur through the fulcrum. This arrangement may ensure stability of the protection plate 408 during a procedure. When the nozzle 406 ejects water or a water mixture, a force may be imparted by the ejecta onto the protection plate 408. The protection plate 408 may be made of a material, such as metal (e.g., steel), which withstands the force of the ejecta (e.g., does not bend, does not break, does not lose integrity, does not allow the ejecta to pass through it, does not move, or the like). In an example, the protection plate 408 may be placed near or affixed to a suction line of a fluid waste management system or a waterjet abrasive recycler to collect ejecta from the nozzle 406, such as after the ejecta contacts the protection plate 408.

Figure 5A:
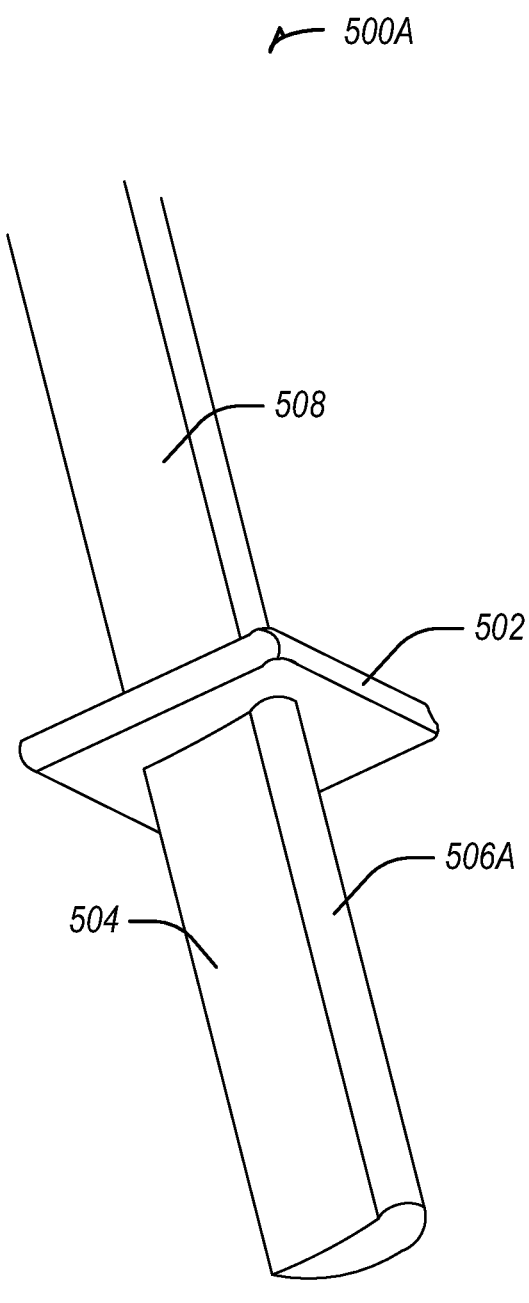
FIG. 5 illustrate close-up views of portions of example waterjet cutting devices including nozzles in accordance with some embodiments.
Figure 5B:
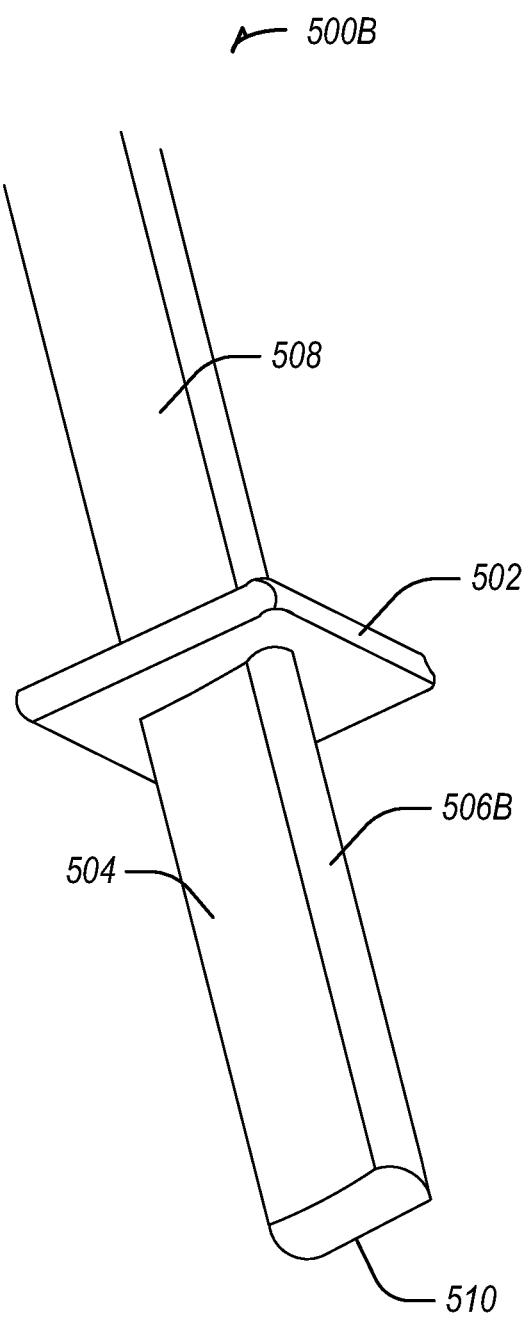

FIG. 5 illustrate close-up views of portions of example waterjet cutting devices including nozzles 500A-500B in accordance with some embodiments. FIG. 5A illustrates a waterjet cutting device including a nozzle 500A with a flat portion 504 and an optional rounded portion 506A. FIG. 5B illustrates the nozzle 500B with a first flat portion 504, an optional rounded portion 506B, and a second flat portion 510, an edge of which is shown in view 500B. The waterjet cutting devices may include a guard component 502 to prevent the nozzle 500A or 500B from inserting too far into a slot of a cut guide.

The flat portion 504 of nozzle 500A or the flat portions 504 and 510 of nozzle 500B may be used to improve performance of the nozzles 500A-500B with a cut guide (e.g., a 3D printed cut guide). The cut guide may include one or more slots, into which the nozzles 500A-500B may be inserted. When inserting a nozzle, the nozzle may rotate within a slot. To prevent this rotation, the flat portions flat portion 504 of nozzle 500A or the flat portions 504 and 510 of nozzle 500B may be used to be in contact with a side wall of the slot. The flat plane or planes of the nozzles 500A-500B may not rotate when in contact with the side wall of the slot of the cut guide. In an example, the single flat portion 504 of nozzle 500A may be sufficient to prevent rotation of the nozzle 500A. In another example, the two flat portions 504 and 510 of nozzle 500B may provide additional or redundant rotation prevention, for example by having flat portion 504 in contact with a first side wall and flat portion 510 in contact with a second side wall of a slot.

The design of the nozzles 500A-500B may provide additional control when operating the waterjet cutting devices. For example, the flat portion 504 or the flat portion 510 (of FIG. 5B) may allow controlled sliding along a slot, or rotation (angulation) within a slot (e.g., along the slot axis rather than the prevented torsional rotation). The controlled sliding or rotation may allow a waterjet cutting device to cut additional portion of bone without needing to switch to a new slot or remove the nozzle and reinsert the nozzle, while simultaneously preventing the waterjet cutting device from inadvertently cutting an unintended portion of bone, soft tissue, or other patient anatomy.

Figure 6:
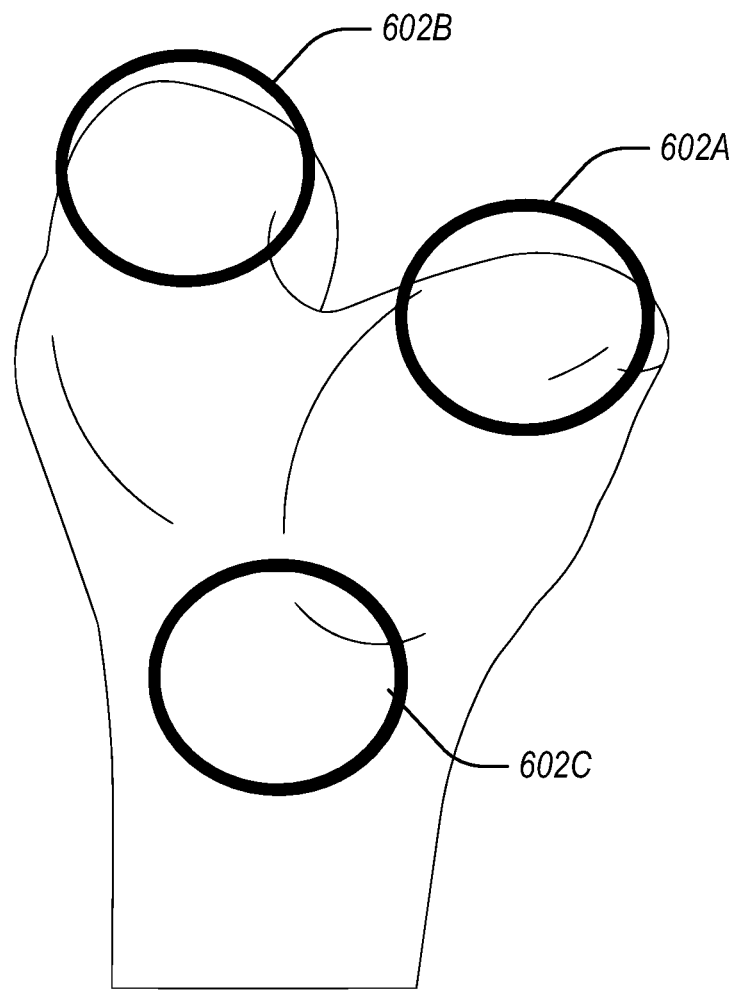
FIG. 6 illustrates a target bone to be cut using a waterjet cutting system in accordance with some embodiments.

FIG. 6 illustrates a target bone 600 to be cut using a waterjet cutting system in accordance with some embodiments. The target bone includes three feature points 602A, 602B, and 602C. The feature points may be used as reference points to create a model of the target bone 600, such that a cut guide model may be customized to the target bone 600. The cut guide model may then be used to 3D print a cut guide to be used on the target bone 600. The feature points may include a high point of a medial condyle 602A, a high point of a lateral condyle 602B, or a high point of an anterior condyle 602C of a distal femur.

When creating the model for the cut guide based on the feature points 602A-602C, the cut guide may be custom fit to the bone 600. The feature points 602A-602C may be further used as reference points to complete a characteristic osteotomy on the bone 600. To place the cut guide on the bone 600, the feature points 602A-602C may be used. After the cut guide is located on the distal femur using the feature points 602A-602C, the cut guide may be fixed to the bone 600, such as by using pins or screws. For example, the pins may include two Nexgen Hex Head Holding pins. In another example, the feature points may include areas of the bone 600 where the collateral ligaments (medial or lateral) attach to the bone 600.

Figure 7:
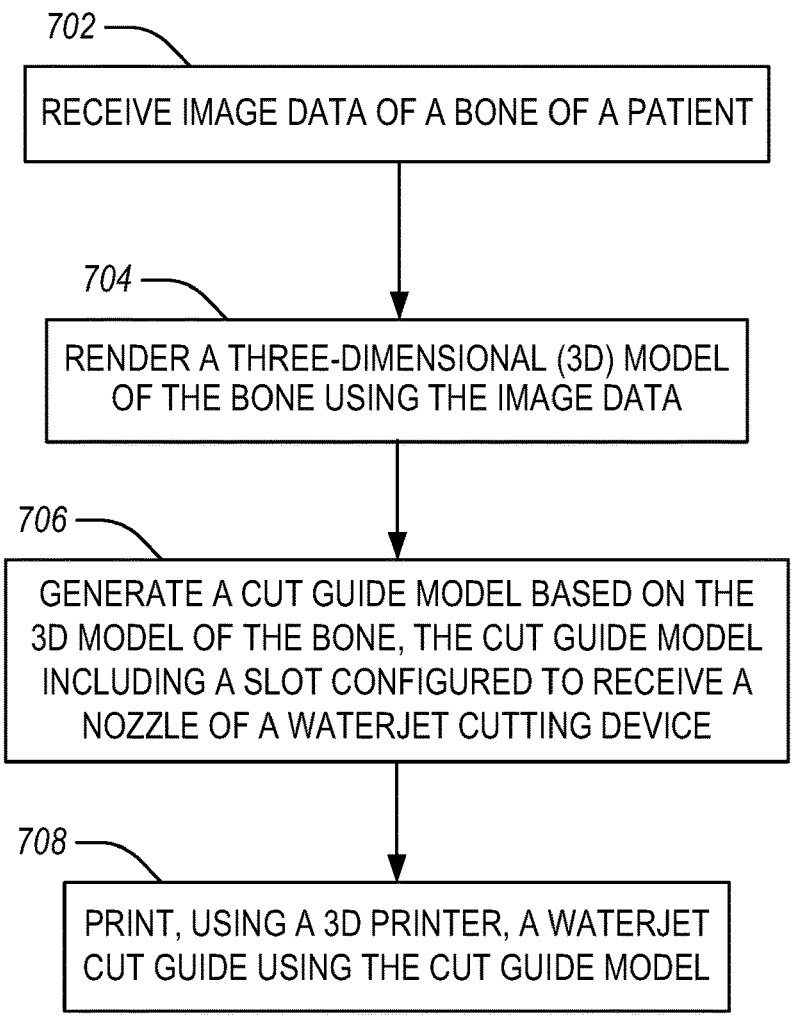
FIG. 7 illustrates a flow chart showing a technique for generating a waterjet cutting system in accordance with some embodiments.

FIG. 7 illustrates a flow chart showing a technique 700 for generating a waterjet cutting system in accordance with some embodiments. The operations of the technique 700 may be performed using a processor. For example, the technique may include instructions included on memory, which when executed by a processor, cause the processor to perform the operations. The technique 700 includes an operation 702 to receive image data, for example from an X-Ray, a CT scan, or an MRI, of a bone of a patient.

The technique 700 includes an operation 704 to render a three-dimensional (3D) model of the bone using the image data. Operation 704 may include rendering the 3D model of the bone includes using reference points from the image data of the bone. The reference points may include condyles, such as a medial, lateral, or anterior condyle of a distal femur. In an example, the bone is a femur, and the reference points include a high point of a medial condyle, a high point of a lateral condyle, and a high point of an anterior condyle of the bone.

The technique 700 includes an operation 706 to generate a cut guide model based on the 3D model of the bone, the cut guide model including a slot configured to receive a nozzle of a waterjet cutting device. Operation 706 may include generating the cut guide model using data measured from the patient. The measured data may include a bone size or an angle of alignment of the bone. In an example, the nozzle includes a flat portion such that the flat portion rests against a wall of the slot to prevent rotation (relative to the wall) of the nozzle when in use. Other rotation, such as along the slot may be permitted. The nozzle may include two flat portions, opposite one another such that the flat portions rest against opposite walls of the slot.

The technique 700 includes an operation 708 to print, using a 3D printer, a waterjet cut guide using the cut guide model. The 3D printer may be used to print the waterjet cut guide with a plurality of pin holes, the plurality of pin holes configured to receive pins to secure the waterjet cut guide to the bone. In an example, printing the waterjet cut guide includes with a plurality of slots. The plurality of slots may each be configured to receive the nozzle to allow the waterjet cutting device to perform a plurality of resections on the bone, such as without the waterjet cut guide being moved (e.g., removed from the slot, removed from contact with the slot, or inserted into a new slot). In an example, the waterjet cut guide may be printed in plastic or metal. The waterjet cut guide may be printed in a single piece, in at least two pieces, such as a lateral and a medial piece or an anterior and a posterior piece, or the like. The waterjet cut guide may be printed with a plate to guard portions of the bone or other patient anatomy from being cut by the waterjet cutting device. The plate may be separately printed, manufactured, or generated, or may be 3D printed as a single piece or part of a set with the waterjet cut guide.

In an example, the technique 700 includes displaying, using a display device, the cut guide model and the 3D model of the bone. For example, the cut guide model may be shown such that modifications may be made, for example according to a procedure to be performed (e.g., a total knee arthroplasty versus a partial knee arthroplasty, which may have differing slot positions or slot lengths). For example, for a partial knee arthroplasty, the plurality of slots may be substantially present on a side (e.g., medial or lateral) of the waterjet cut guide, while not substantially not appearing on the opposite side, although some portion of a slot may extend into the opposite side for ease of use on the side where cutting is to occur.

Figure 8:
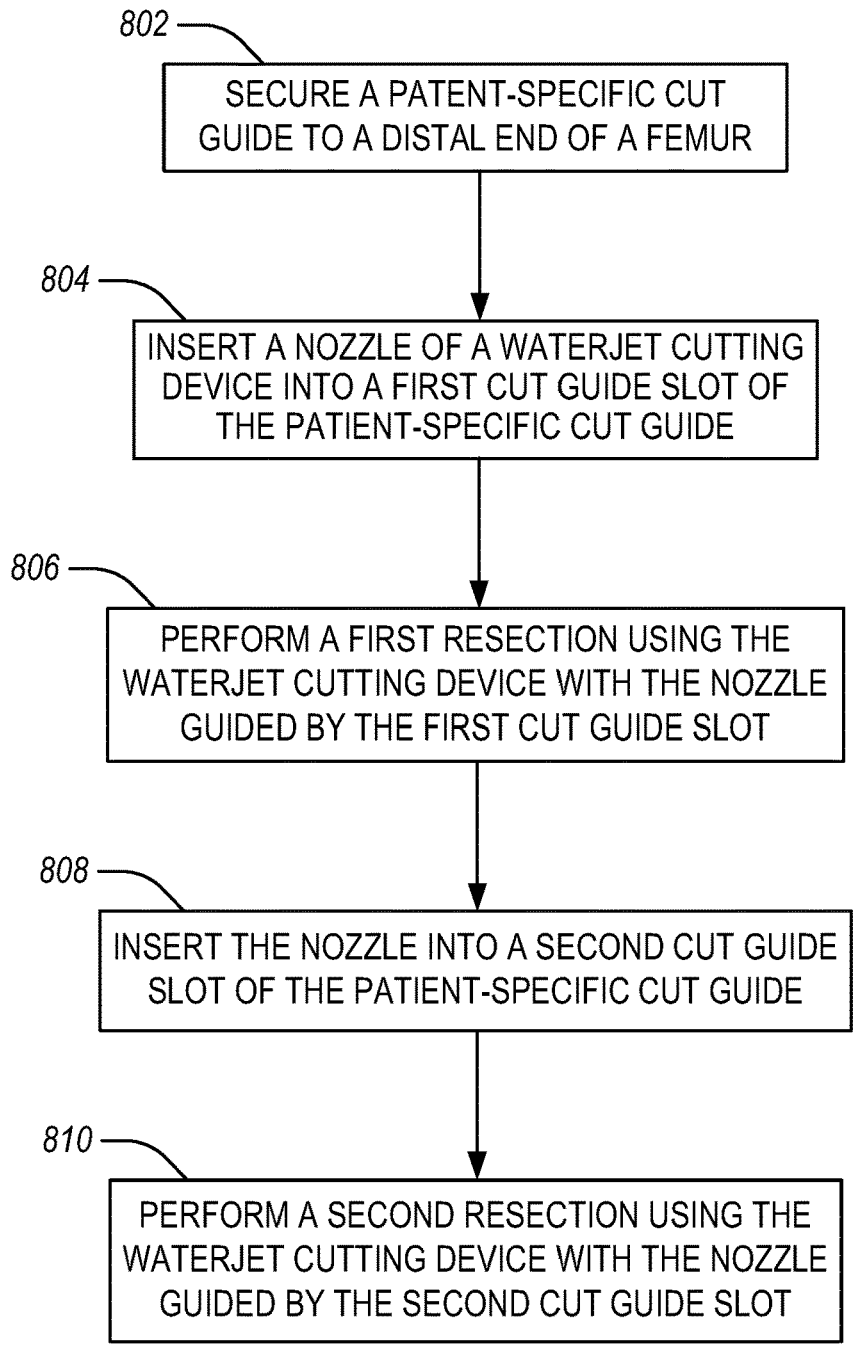
FIG. 8 illustrates a flow chart showing a technique 800 for using a patient-specific cut guide and waterjet system to resect a distal end of a femur in accordance with some embodiments.

FIG. 8 illustrates a flow chart showing a technique 800 for using a patient-specific cut guide and waterjet system to resect a distal end of the femur in accordance with some embodiments. The technique 800 includes an operation 802 to secure a patent-specific cut guide to a distal end of the femur. The operation 802 may include securing the patient-specific cut guide to the femur using pins, screws, etc. The patient-specific cut guide may be a 3D-printed cut guide. The 3D-printed cut guide may be printed from a cut guide model that may be generated based on a model of the distal end of the femur. The model of the distal end of the femur may be generated from one or more images, such as from a CT-scan, an MRI, or an x-ray.

The technique 800 includes an operation 804 to insert a nozzle of a waterjet cutting device into a first cut guide slot of the patient-specific cut guide. The technique 800 includes an operation 806 to perform a first resection using the waterjet cutting device with the nozzle guided by the first cut guide slot. To perform the first resection, a surgeon may activate the nozzle to eject water or a water mixture. For example, the nozzle may be computer-controlled, and the surgeon may activate the nozzle using a user interface, which in turn may cause the computer to control the nozzle to activate. In another example, the waterjet cutting device may have an apparatus to control a valve to activate the nozzle. The nozzle may expel a pressurized cutting fluid in a defined shape.

The technique 800 includes an operation 808 to insert the nozzle into a second cut guide slot of the patient-specific cut guide. The technique 800 includes an operation 810 to perform a second resection using the waterjet cutting device with the nozzle guided by the second cut guide slot.

The technique 800 may include an optional operation to position a guard to receive ejecta from waterjet nozzle after resection. The guard may include a plate to block the ejecta from contacting a bone or soft tissue anatomy of a patient. The technique 800 may include performing additional resections using additional cut guide slots of the patient-specific cut guide until all resections to be performed during a knee arthroplasty (e.g., total or partial) have been completed.

In an example the technique 800 may include removing or disposing of ejecta (e.g., water or a water-mixture or fluids or materials from the patient) from the waterjet nozzle. For example, a floor drain may be installed in the floor of the surgical field to receive the ejecta. In an example, a waterjet abrasive material recycling or reclamation may be performed to retrieve the mixture portion of the ejecta. In another example, a fluid waste management system may be used to remove the ejecta from the surgical field. For example, a fluid waste management system manufactured by Zimmer Inc. of Warsaw, Ind. may be used. In an example, the fluid waste management system may be one described in U.S. Pat. No. 6,893,425, titled "High Volume Liquid Waste Collection And Disposal System," which is hereby incorporated herein in its entirety. A fluid waste management system may be connected to the guard positioned to receive ejecta from the waterjet nozzle after resection. For example, a suction line may be positioned near the guard or affixed to the guard to collect the ejecta, for example after the ejecta hits the guard.

Figure 9:
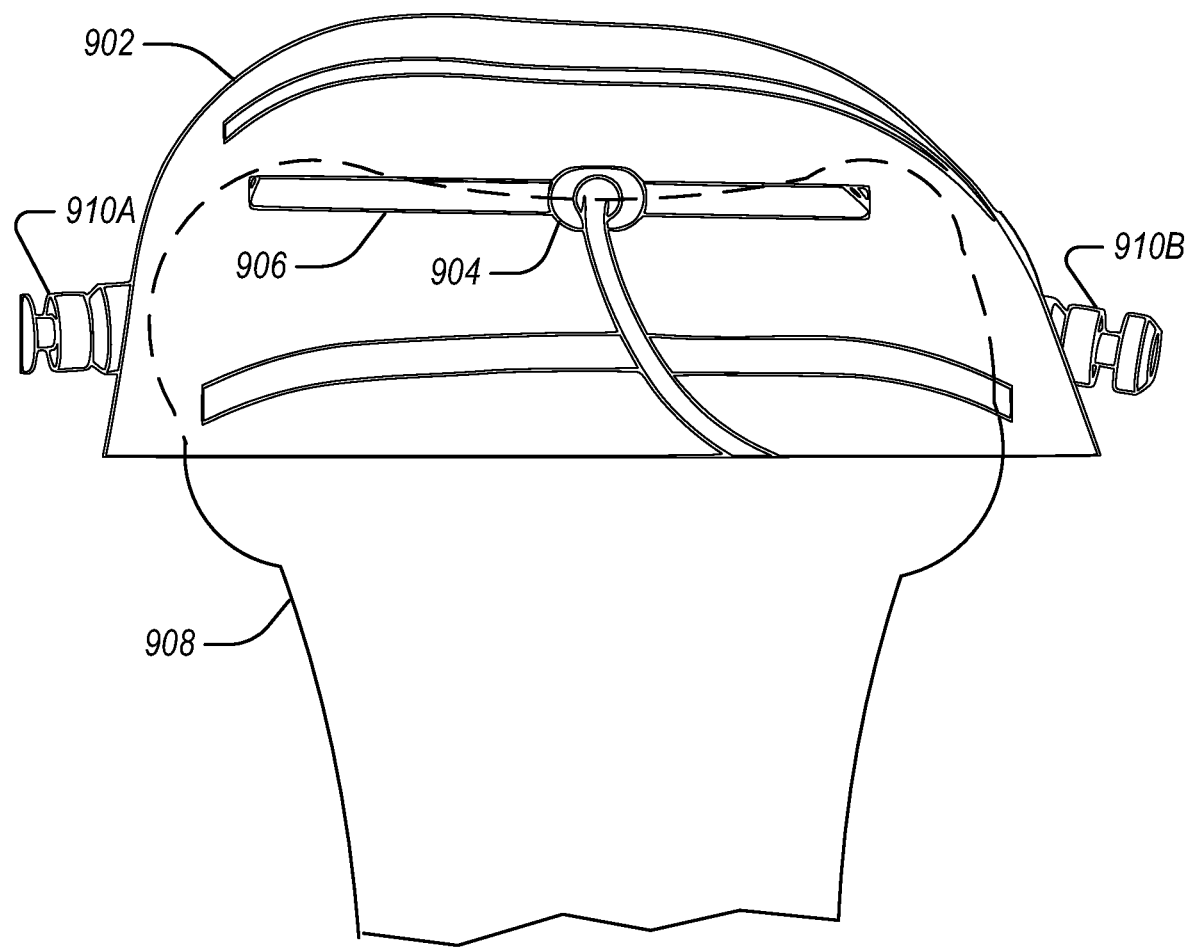
FIG. 9 illustrates a tibial cut guide for use in a waterjet cutting system in accordance with some embodiments.

FIG. 9 illustrates a tibial cut guide 902 for use in a waterjet cutting system 900 in accordance with some embodiments. The tibial cut guide 902 may be used with a waterjet cutting system, including a waterjet nozzle 904. The nozzle 904 may be inserted into a slot 906 of the tibial cut guide 902 to perform a resection of a tibia 908, such as a proximal tibial resection during a knee arthroplasty. Though a plurality of slots (e.g., slot 906) are shown on the tibial cut guide 902, in an example the tibial cut guide 902 may include only one slot 904. The tibial cut guide 902 may be secured to the tibia 908 using pins, screws, etc., such as pins 910A and 910B. In another example, the tibial cut guide 902 may be secured to the tibia 908 using friction (e.g., by compression on the tibia 908). The tibial cut guide 902 may be a tibial version of the various cut guides described above, for example, including features discussed above with respect to FIGS. 1-4 (which, by way of example, show a femoral cut guide).

Figure 10:
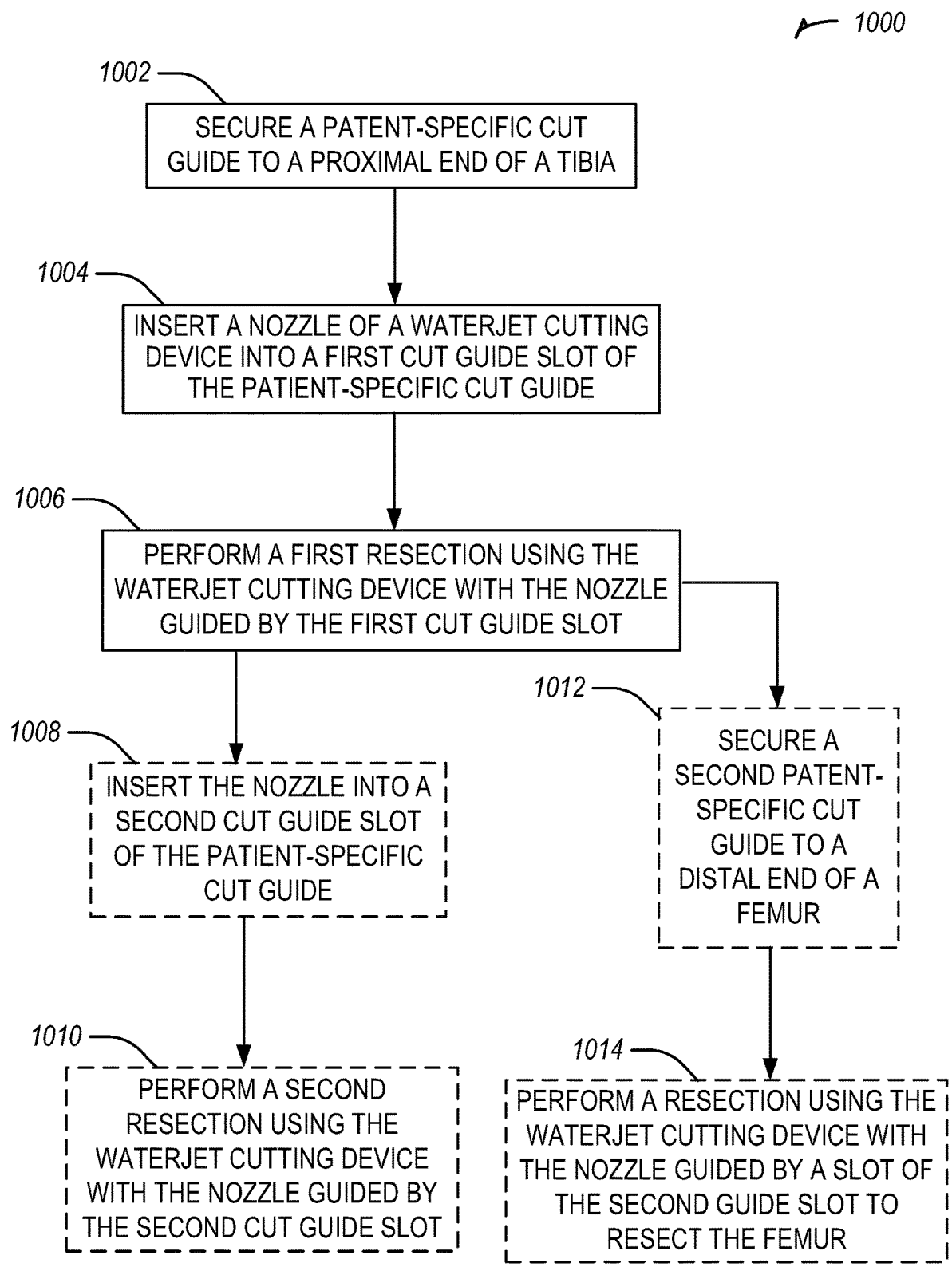
FIG. 10 illustrates a flow chart showing a technique for using a waterjet cutting system to resect a tibia in accordance with some embodiments.

FIG. 10 illustrates a flow chart showing a technique 1000 for using a waterjet cutting system to resect a tibia in accordance with some embodiments. The technique 1000 includes an operation 1002 to secure a patent-specific cut guide to a proximal end of a tibia. The operation 1002 may include securing the patient-specific cut guide to the tibia using pins, screws, etc. The patient-specific cut guide may be a 3D-printed cut guide. The 3D-printed cut guide may be printed from a cut guide model that may be generated based on a model of the proximal end of the tibia. The model of the proximal end of the tibia may be generated from one or more images, such as from a CT-scan, an MRI, or an x-ray.

The technique 1000 includes an operation 1004 to insert a nozzle of a waterjet cutting device into a first cut guide slot of the patient-specific cut guide. The technique 1000 includes an operation 1006 to perform a first resection using the waterjet cutting device with the nozzle guided by the first cut guide slot. To perform the first resection, a surgeon may activate the nozzle to eject water or a water mixture. For example, the nozzle may be computer-controlled, and the surgeon may activate the nozzle using a user interface, which in turn may cause the computer to control the nozzle to activate. In another example, the waterjet cutting device may have an apparatus to control a valve to activate the nozzle. The nozzle may expel a pressurized cutting fluid in a defined shape.

The technique 1000 includes an optional operation 1008 to insert the nozzle into a second cut guide slot of the patient-specific cut guide. The technique 1000 includes an optional operation 1010 to perform a second resection using the waterjet cutting device with the nozzle guided by the second cut guide slot, for example in response to inserting the nozzle into the second cut guide slot.

The technique 1000 includes an optional operation 1012 to secure a second patent-specific cut guide to a distal end of a femur. The technique 1000 includes an optional operation 1014 to perform a resection using the waterjet cutting device with the nozzle guided by a slot of the second guide slot to resect the femur. In an example, the operations 1012 and 1014 may be performed before operation 1002, 1004, 1006, 1008, or 1010. For example, a femoral cut may be made before or after a tibial cut.

Figure 11:
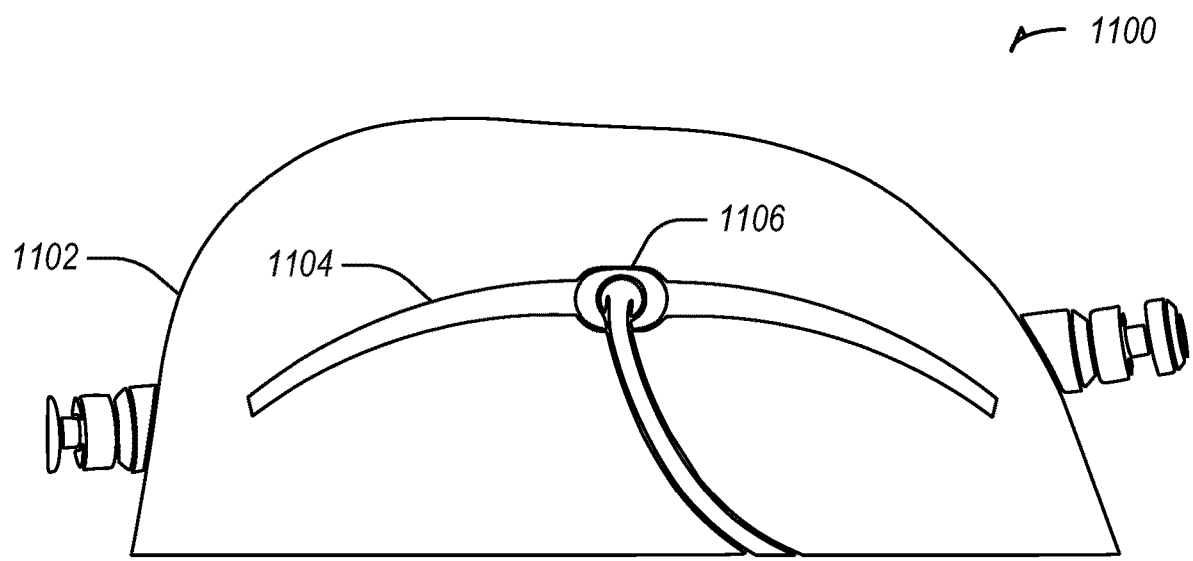
FIG. 11 illustrates cut guide including a curved slot for use with a waterjet cutting system in accordance with some embodiments.

FIG. 11 illustrates cut guide 1102 including a curved slot 1104 for use with a waterjet cutting system 1100 in accordance with some embodiments. The curved slot 1104 may be used to resect a femur or tibia to create a curved surface on the femur or the tibia, such as by activating a waterjet cutting device having a nozzle 1106 inserted into the curved slot 1104. The waterjet cutting system 110 may be used, for example, to prepare a bone for a curved implant. By using the curved slot 1104 to create the curved surface, a procedure may result in less bone resection, improved biomechanics for the bone, improved structure of knee prosthesis for strength, improved fixture of the implant after implantation, or the like, than results obtained using a straight slot.

Example 1 is a method for printing a waterjet cut guide comprising: receiving, at a processor, image data of a bone of a patient; rendering, using the processor, a three-dimensional (3D) model of the bone using the image data; generating, using the processor, a cut guide model based on the 3D model of the bone, the cut guide model including a slot configured to receive a nozzle of a waterjet cutting device; and printing, using a 3D printer, a waterjet cut guide using the cut guide model.

In Example 2, the subject matter of Example 1 includes, 3D model of the bone includes using reference points from the image data of the bone.

In Example 3, the subject matter of Example 2 includes, wherein the bone is a femur, and wherein the reference points include a high point of an medial condyle, a high point of an lateral condyle, and a high point of an anterior condyle of the bone.

In Example 4, the subject matter of Examples 1-3 includes, wherein generating the cut guide model includes using data measured from the patient.

In Example 5, the subject matter of Example 4 includes, wherein the measured data includes a bone size or an angle of alignment of the bone.

In Example 6, the subject matter of Examples 1-5 includes, wherein printing the waterjet cut guide includes printing the waterjet cut guide with a plurality of pin holes, the plurality of pin holes configured to receive pins to secure the waterjet cut guide to the bone.

In Example 7, the subject matter of Examples 1-6 includes, wherein printing the waterjet cut guide includes printing the waterjet cut guide with a plurality of slots.

In Example 8, the subject matter of Example 7 includes, wherein the plurality of slots are each configured to receive the nozzle to allow the waterjet cutting device to perform a plurality of resections on the bone without the waterjet cut guide being moved.

In Example 9, the subject matter of Examples 1-8 includes, 3D model of the bone.

In Example 10, the subject matter of Examples 1-9 includes, wherein the nozzle includes a flat portion such that the flat portion rests against a wall of the slot to prevent rotation of the nozzle when in use.

In Example 11, the subject matter of Examples 1-10 includes, wherein printing the waterjet cut guide includes printing the waterjet cut guide in plastic or metal.

In Example 12, the subject matter of Examples 1-11 includes, wherein printing the waterjet cut guide includes printing the waterjet cut guide in a single piece.

In Example 13, the subject matter of Examples 1-12 includes, wherein printing the waterjet cut guide includes printing the waterjet cut guide in at least two pieces, wherein the at least two pieces include a lateral and a medial piece or an anterior and a posterior piece.

Example 14 is at least one machine-readable medium including instructions for operation of a computing system, which when executed by a machine, cause the machine to perform operations of any of the methods of Examples 1-13.

Example 15 is a system for printing a waterjet cut guide comprising: a processor coupled to memory including instructions for preparing the waterjet cut guide, which when executed by a processor, cause the processor to: receive image data of a bone of a patient; render a three-dimensional (3D) model of the bone using the image data; and generate a cut guide model based on the 3D model of the bone, the cut guide model including a slot configured to receive a nozzle of a waterjet cutting device; and a 3D printer to print the waterjet cut guide using the cut guide model.

In Example 16, the subject matter of Example 15 includes, 3D model of the bone, the memory includes instructions to cause the processor to use reference points from the image data of the bone.

In Example 17, the subject matter of Example 16 includes, wherein the bone is a femur, and wherein the reference points include a high point of an medial condyle, a high point of an lateral condyle, and a high point of an anterior condyle of the bone.

In Example 18, the subject matter of Examples 15-17 includes, wherein to generate the cut guide model, the memory includes instructions to cause the processor to use data measured from the patient.

In Example 19, the subject matter of Example 18 includes, wherein the measured data includes a bone size or an angle of alignment of the bone.

In Example 20, the subject matter of Examples 15-19 includes, 3D printer is to print the waterjet cut guide with a plurality of pin holes, the plurality of pin holes configured to receive pins to secure the waterjet cut guide to the bone.

In Example 21, the subject matter of Examples 15-20 includes, 3D printer is to print the waterjet cut guide with a plurality of slots.

In Example 22, the subject matter of Example 21 includes, wherein the plurality of slots are each configured to receive the nozzle to allow the waterjet cutting device to perform a plurality of resections on the bone without the waterjet cut guide being moved.

In Example 23, the subject matter of Examples 15-22 includes, 3D model of the bone.

In Example 24, the subject matter of Examples 15-23 includes, wherein the nozzle includes a flat portion such that the flat portion rests against a wall of the slot to prevent rotation of the nozzle when in use.

In Example 25, the subject matter of Examples 15-24 includes, 3D printer is to print the waterjet cut guide in plastic or metal.

In Example 26, the subject matter of Examples 15-25 includes, 3D printer is to print the waterjet cut guide in a single piece.

In Example 27, the subject matter of Examples 15-26 includes, 3D printer is to print the waterjet cut guide in at least two pieces, wherein the at least two pieces include a lateral and a medial piece or an anterior and a posterior piece.

In Example 28, the subject matter of Examples 15-27 includes, wherein the system further comprises a metal plate configured to prevent the waterjet cutting device from cutting anatomy of the patient other than the bone.

In Example 29, the subject matter of Examples 15-28 includes, wherein the waterjet cutting device cuts the bone using water or a water-cement mixture.

Example 30 is at least one non-transitory machine-readable medium including instructions for preparing a waterjet cut guide, which when executed by a machine, cause the machine to: receive image data of a bone of a patient; render a three-dimensional (3D) model of the bone using the image data; and generate a cut guide model based on the 3D model of the bone, the cut guide model including a slot configured to receive a nozzle of a waterjet cutting device; and output, to a 3D printer for printing, the waterjet cut guide using the cut guide model.

In Example 31, the subject matter of Example 30 includes, 3D model of the bone, the instructions are further to cause the processor to use reference points from the image data of the bone.

In Example 32, the subject matter of Example 31 includes, wherein the bone is a femur, and wherein the reference points include a high point of an medial condyle, a high point of an lateral condyle, and a high point of an anterior condyle of the bone.

In Example 33, the subject matter of Examples 30-32 includes, wherein to generate the cut guide model, the instructions are further to cause the processor to use data measured from the patient.

In Example 34, the subject matter of Example 33 includes, wherein the measured data includes a bone size or an angle of alignment of the bone.

In Example 35, the subject matter of Examples 30-34 includes, wherein to output the waterjet cut guide, the instructions are further to cause the processor to output the waterjet cut guide with a plurality of pin holes, the plurality of pin holes configured to receive pins to secure the waterjet cut guide to the bone.

In Example 36, the subject matter of Examples 30-35 includes, wherein to output the waterjet cut guide, the instructions are further to cause the processor to output the waterjet cut guide with a plurality of slots.

In Example 37, the subject matter of Example 36 includes, wherein the plurality of slots are each configured to receive the nozzle to allow the waterjet cutting device to perform a plurality of resections on the bone without the waterjet cut guide being moved.

In Example 38, the subject matter of Examples 30-37 includes, 3D model of the bone.

In Example 39, the subject matter of Examples 30-38 includes, wherein the nozzle includes a flat portion such that the flat portion rests against a wall of the slot to prevent rotation of the nozzle when in use.

In Example 40, the subject matter of Examples 30-39 includes, wherein to output the waterjet cut guide, the instructions are further to cause the processor to output the waterjet cut guide including an indication to print the waterjet cut guide in plastic or metal.

In Example 41, the subject matter of Examples 30-40 includes, wherein to output the waterjet cut guide, the instructions are further to cause the processor to output the waterjet cut guide in a single piece.

In Example 42, the subject matter of Examples 30-41 includes, wherein to output the waterjet cut guide, the instructions are further to cause the processor to output the waterjet cut guide including an indication to print the waterjet cut guide in at least two pieces, wherein the at least two pieces include a lateral and a medial piece or an anterior and a posterior piece.

Example 43 is a waterjet resection system comprising: a patient-specific cut guide including a plurality of cut guide slots adapted to receive a waterjet nozzle; the waterjet nozzle including a distal end adapted to expel a pressurized cutting fluid in a defined shape; a control system configured to enable controlled cutting with the waterjet nozzle.

In Example 44, the subject matter of Example 43 includes, 3D model of a bone to be cut.

In Example 45, the subject matter of Examples 43-44 includes, 3D model of the bone is generated using image data of the bone.

In Example 46, the subject matter of Examples 43-45 includes, wherein the patient-specific cut guide includes at least one pin hole to secure the patient-specific cut guide to a bone to be cut using at least one pin.

In Example 47, the subject matter of Examples 43-46 includes, wherein the waterjet nozzle includes a flat portion such that the flat portion rests against respective walls of the plurality of cut guide slots when inserted to prevent rotation of the waterjet nozzle when in use.

In Example 48, the subject matter of Examples 43-47 includes, wherein the waterjet resection system further comprises a guard configured to receive ejecta from the waterjet nozzle after a resection is performed.

In Example 49, the subject matter of Examples 43-48 includes, wherein the pressurized cutting fluid is water or a water-cement mixture.

Example 50 is a method for using a patient-specific cut guide and waterjet system to resect a distal end of the femur, the method comprising: securing a patent-specific cut guide to a distal end of the femur inserting a nozzle of a waterjet cutting device into a first cut guide slot of the patient-specific cut guide; performing a first resection using the waterjet cutting device with the nozzle guided by the first cut guide slot; inserting the nozzle into a second cut guide slot of the patient-specific cut guide; and performing a second resection using the waterjet cutting device with the nozzle guided by the second cut guide slot.

In Example 51, the subject matter of Example 50 includes, D-printed cut guide and wherein securing the patient-specific cut guide to the femur includes pinning the patient-specific cut guide to the femur.

In Example 52, the subject matter of Examples 50-51 includes, wherein performing the first and second resections includes activating, using a control system, the nozzle to expel a pressurized cutting fluid in a defined shape.

In Example 53, the subject matter of Examples 50-52 includes, positioning a guard to receive ejecta from the waterjet nozzle after resection.

Example 54 is at least one machine-readable medium including instructions that, when executed by processing circuitry, cause the processing circuitry to perform operations to implement of any of Examples 1-53.

Example 55 is an apparatus comprising means to implement of any of Examples 1-53.

Example 56 is a system to implement of any of Examples 1-53.

Example 57 is a method to implement of any of Examples 1-53.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for printing a waterjet cut guide comprising:
   a nozzle for a waterjet cutting device;
   a processor coupled to memory including instructions for preparing the waterjet cut guide, which when executed by a processor, cause the processor to:
   receive image data of a bone of a patient, the image data being personalized to the patient;
   render a three-dimensional (3D) model of the bone using the image data; and
   generate a cut guide model based on the 3D model of the bone, the cut guide model including a slot configured to receive the nozzle of a waterjet cutting device, wherein the cut guide is a patient-specific cut guide made according to the personalized image data; and
   a 3D printer to print the waterjet cut guide using the cut guide model, wherein the cut guide model includes at least one a slot configured to receive a nozzle of a waterjet cutting device.

2. The system of claim 1, wherein to render the 3D model of the bone, the memory includes instructions to cause the processor to use reference points from the image data of the bone.

3. The system of claim 2, wherein the bone is a femur, and wherein the reference points include a high point of an medial condyle, a high point of an lateral condyle, and a high point of an anterior condyle of the bone.

4. The system of claim 2, wherein to generate the cut guide model, the memory includes instructions to cause the processor to use data measured from the patient.

5. The system of claim 4, wherein the measured data includes a bone size or an angle of alignment of the bone.

6. The system of claim 2, wherein to print the waterjet cut guide, the 3D printer is to print the waterjet cut guide in a single piece.

7. The system of claim 2, wherein to print the waterjet cut guide, the 3D printer is to print the waterjet cut guide in at least two pieces, wherein the at least two pieces include a lateral and a medial piece or an anterior and a posterior piece.

8. At least one non-transitory machine-readable medium including instructions for preparing a waterjet cut guide as for claim 1, which when executed by a machine, cause the machine to: receive image data of a bone of a patient, the image data being personalized to the patient, render a three-dimensional (3D) model of the bone using the image data; and generate a cut guide model based on the 3D model of the bone, the cut guide model including a slot configured to receive a nozzle of a waterjet cutting device, wherein the cut guide is a patient-specific cut guide made according to the personalized image data; output, to a 3D printer for printing, the waterjet cut guide using the cut guide model, output the waterjet cut guide with a plurality of pin holes, the plurality of pin holes configured to receive pins to secure the waterjet cut guide to the bone; and output the waterjet cut guide with a plurality of slots, the plurality of slots each configured to receive the nozzle to allow the waterjet cutting device to perform a plurality of resections on the bone.

* * * * *